US00PP36379P2

(12) United States Plant Patent
Meilland

(10) Patent No.: US PP36,379 P2
(45) Date of Patent: Jan. 14, 2025

(54) BEDDING ROSE PLANT NAMED 'MEILEGASE'

(50) Latin Name: *Rosa hybrida*
Varietal Denomination: MEILEGASE

(71) Applicant: The Conard Pyle Company, West Grove, PA (US)

(72) Inventor: Alain Antoine Meilland, Antibes (FR)

(73) Assignee: The Conard Pyle Company, West Grove, PA (US)

( * ) Notice: Subject to any disclaimer, the term of this patent is extended or adjusted under 35 U.S.C. 154(b) by 39 days.

(21) Appl. No.: 18/400,292

(22) Filed: Dec. 29, 2023

(30) Foreign Application Priority Data

Aug. 9, 2023 (QZ) ..... PBR 2023/1652

(51) Int. Cl.
*A01H 5/02* (2018.01)
*A01H 6/74* (2018.01)

(52) U.S. Cl.
USPC ..... Plt./101
CPC ..... *A01H 6/749* (2018.05)

(58) Field of Classification Search
USPC ..... Plt./101
CPC ..... A01H 6/749; A01H 5/02
See application file for complete search history.

(56) References Cited

U.S. PATENT DOCUMENTS

PP9,469 P 3/1996 Meilland
PP12,125 P2 10/2001 Olesen et al.

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of bedding rose plant, referred to by its cultivar name, 'MEILEGASE', is disclosed. The new variety forms attractive, semi-double, pink colored flowers. Attractive rather dense, semi-glossy foliage is formed, which contrasts beautifully with the blossoms. A bushy growth habit is displayed. The new variety is well suited for providing attractive ornamentation in the landscape.

1 Drawing Sheet

Latin name of genus and species of plant claimed: *Rosa hybrida.*

Variety denomination: 'MEILEGASE'.

CROSS REFERENCE TO RELATED APPLCIATIONS

This application claims priority to Plant Breeders' Right Application Number 2023/1652, which was filed at Community Plant Variety Office in the European Union on Aug. 9, 2023, the contents of which are hereby incorporated by reference for all purposes.

STATEMENT REGARDING PRIOR DISCLOSURES BY THE INVENTOR

The first offer for sale of the new variety was Jan. 5, 2023, in France. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was the 'POULweeto' variety (U.S. Plant Pat. No. 12,125). The male parent (i.e., the pollen parent) of the new variety was an unnamed seedling (not patented).

The parentage of the new variety can be summarized as follows:

'POULweeto' X Unnamed Seedling

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms pink colored flowers,
(b) produces semi-double flowers, and
(c) exhibits a bushy growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'POULweeto' variety (i.e., the seed parent) exhibits a lighter pink colored flower compared to flowers of the new variety. In addition, the unnamed seedling male parent (i.e., pollen parent) exhibits white colored flowers, whereas the new variety exhibits pink colored flowers. Moreover, the new variety can be readily distinguished from other similar non-parental varieties. For example, the 'Meibonrib' variety (U.S. Plant Pat. No. 9,469) is a groundcover variety with glossy foliage and forms a much bigger plant compared to the new variety, which provides semi-glossy foliage.

The new variety has been named 'MEILEGASE'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately two years of age and were observed during September while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms and The R.H.S. Colour Chart designation used herein represents the closest color observed on the majority of the specified botanical feature. The description is based on the observation of two-years-old specimens of the new variety during September while budded on their own roots and growing outdoors at Le Cannet des Maures, Var, France.

Botancal classification: *Rosa hybrida* cultivar 'MEILEGASE'.

Commercial classification: Bedding Rose Plant.

Plant:

*Habit*.—Bushy.

*Height*.—Approximately 50 cm on average.

*Width*.—Approximately 90 cm on average.

Branches:

*Color*.—Young stems: commonly Yellow-Green Group 144A slightly suffused with Greyed-Red Group 178A. Adult wood: commonly Green Group 138A.

*Length*.—From the crown to the flower is typically between 15 cm to 45 cm.

*Diameter*.—Typically between 0.2 cm to 1.2 cm.

*Thorns*.—Configuration on adult stems: flat, elongated and curved downwards on the upper surface and very concave on the under surface. Long prickles — quantity: approximately 5 thorns on average per 10 cm long young stem and approximately 7 thorns on average per 10 cm long adult stem. Long prickles — length: typically between 0.4 cm to 0.5 cm on young stems and typically between 0.5 cm to 0.8 cm on adult stems. Long prickles — width at base: typically between 0.5 cm to 0.7 cm on young stems and typically between 0.5 cm to 1.0 cm on adult stems. Long prickles — base shape: oval, narrow, and short on young stems and oval, narrow, and rather short on adult stems. Long prickles — color on young stems: commonly Greyed-Purple Group 185C. Long prickles — color on adult stems: commonly Greyed-Orange Group 165B. Small prickles — quantity: absent.

*Internode*.—Numbers on the entire branch: typically between 4 to 15. Length: typically between 2 cm to 8 cm.

Foliage:

*General appearance*.—Rather dense, dark, semi-glossy.

*Number of leaflets*.—3, 5, 7; most often 5.

5 *leaflets leaf*.—Length: typically between 5.5 cm to 9.0 cm. Width: typically between 3.8 cm to 5.7 cm.

*Terminal leaflet*.—Length: typically between 2.4 cm to 3.5 cm. Width: typically between 1.5 cm to 2.0 cm.

*Young shoots*.—Anthocyanin coloration: commonly Greyed-Purple Group 187A.

*New foliage*.—Upper surface color: commonly Green Group 137B more or less suffused with Greyed-Red Group 178B. Under surface color: commonly Greyed-Purple Group 183B.

*Adult foliage*.—Upper surface color: commonly Green Group 137A. Under surface color: commonly Green Group 138B.

Leaflets:

*Shape*.—Tip: attenuated. Base: cuneiform.

*Intensity of glossiness*.—Light.

*Texture*.—Moderately leathery.

*Smoothness*.—Upper and under surfaces are bumpy.

*General appearance*.—Oboval.

*Serration*.—Small and single.

*Undulation on the margin*.—Very weak.

*Venation*.—Color is commonly Greyed-Yellow Group 160A and pattern is imparipinnate.

*Petiole rachis*.—Color of upper surface: commonly Yellow-Green Group 146B. Color of under surface: commonly Yellow-Green Group 144A. Texture: upper surface is smooth, under surface is small prickles. Rachis of terminal leaflet: length is typically between 1.5 cm to 3.2 cm and diameter is approximately 0.1 cm on average.

*Petioles*.—Upper surface: glandular. Under surface: glandular with small prickles. Color of upper surface: commonly Yellow-Green Group 146B. Color of under surface: commonly Yellow-Green Group 144A. Length: typically between 1.3 cm to 1.7 cm. Diameter: approximately 0.1 cm on average.

*Stipules*.—Length: typically between 1.0 cm to 1.4 cm. Width: approximately 0.1 cm on average. General appearance: narrow. Texture: smooth on upper and under surfaces. Color of upper surface: commonly Yellow-Green Group 146B. Color of under surface: commonly Yellow-Green Group 147B.

Inflorescence:

*Number of flowers per stem*.—Typically between 1 to 50 flowers per stem.

*Lastingness of the bloom*.—On the plant: approximately 7 days. In vase: not tested.

*Bud*.—Shape: conical. Size: small. Length: typically between 1.0 cm to 1.5 cm. Width: typically between 0.8 cm to 1.2 cm. Color as calyx breaks: upper surface: commonly a color between Red Group 45A and Red Group 53A; basal spot is commonly Yellow Group 9A. under surface: commonly Red Group 53A; basal spot is absent.

*Sepals*.—Number: commonly 5. Length: typically between 1.5 cm to 2.3 cm. Width: typically between 0.5 cm to 0.6 cm. Shape: at the top: elongate and narrow. at the base: flat at union with the receptacle. Extensions: typically 2 sepals without extensions, 3 sepals with weak extension; length of extension is typically between 0.2 cm to 1.8 cm; width of extension is typically between 0.1 cm to 0.8 cm. Upper surface: texture: tomentous. color: commonly Green Group 138B. Under surface: texture: glandular. color: commonly Green Group 138A.

*Receptacle*.—Color: commonly Green Group 138B. Length: approximately 0.6 cm on average. Width: approximately 0.4 cm on average. Surface: smooth. Shape: pitcher shaped.

*Peduncle*.—Length: typically between 1.5 cm to 2.5 cm. Width: approximately 0.15 cm on average. Surface: glandular. Color: commonly Yellow-Green Group 144A.

*Flower*.—Diameter when open: typically between 4.5 cm to 5.5 cm. Depth of the flower: typically between 1.5 cm to 2.0 cm. Shape: flat cup shaped. Shape when viewed from above: irregular rounded. Shape of the upper part of the flower profile: cup shape. Shape of the lower part of the flower profile: flat. Type: semi-double. Number of petals under normal conditions: typically between 10 to 20. Petals: shape: obovate (cuspidate at the top and obtuse or attenuated at the base). texture: soft. length: typically between 1.5 cm to 3.0 cm. width: typically between 0.8 cm to 2.3 cm. Undulation of the petal: very weak. Reflexing of the petal: very weak. Petal incision: absent. Petal arrangement: imbricated with few petaloids (sometimes between 1 and 5 petaloids and petaloid shape is deformed petal shape). Petal drop: petals drop off cleanly before drying. Fragrance: none. Discoloration of the flower: very light. Color when opening: basal spot on the upper surface: commonly Yellow Group 9A. upper surface: commonly a color between Red Group 45B and Red Group 53B. basal spot on the under surface: very little, less than 0.1 cm and commonly Yellow Group 9A. under surface: commonly Red Group 53B. Color of the open flower: basal spot on upper surface: commonly Yellow Group 9A. upper surface: commonly Red Group 57C. basal spot on under surface: commonly Yellow Group 9A. under surface of the flower: commonly Red Group 52A. Anthers: approximately 70 on average, length is approximately 0.2 cm on average, width is approximately 0.1 cm on average, coloration is commonly Yellow-Orange Group 17A, and arrangement is regular around styles. Filaments: length is typically between 0.1 cm to 0.5 cm and coloration is commonly Greyed-Orange Group 163A. Styles: length is typically between 0.3 cm to 0.4 cm, coloration is commonly Red Group 46A, and number is approximately 20 on average. Stigmas: length is approximately 0.1 cm on average and coloration is commonly Greyed-Yellow Group 162B. Pollen: medium quantity; color is commonly Yellow-Orange Group 17A. Hips: length is approximately 1.0 cm on average; width is typically between 1.2 cm to 1.3 cm; color is a color between Yellow-Green Group 144A and Yellow-Green Group 146B; mature fruit color is commonly Greyed-Orange Group 176A; and shape is rounded like an apple.

Development:

*Vegetation*.—Strong.

*Blooming*.—Early in the season abundant and nearly continuous, typically from May to November in France.

*USDA hardiness zone*.—Zone 5 to 9.

*Tolerance to disease*.—Good, and particularly against black spot (*Diplocarpon rosae*).

The new 'MEILEGASE' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEILEGASE' characterized by the following combination of characteristics:

(a) forms pink colored flowers, (b) produces semi-double flowers, and (c) exhibits a bushy growth habit;

substantially as herein shown and described.

* * * * *

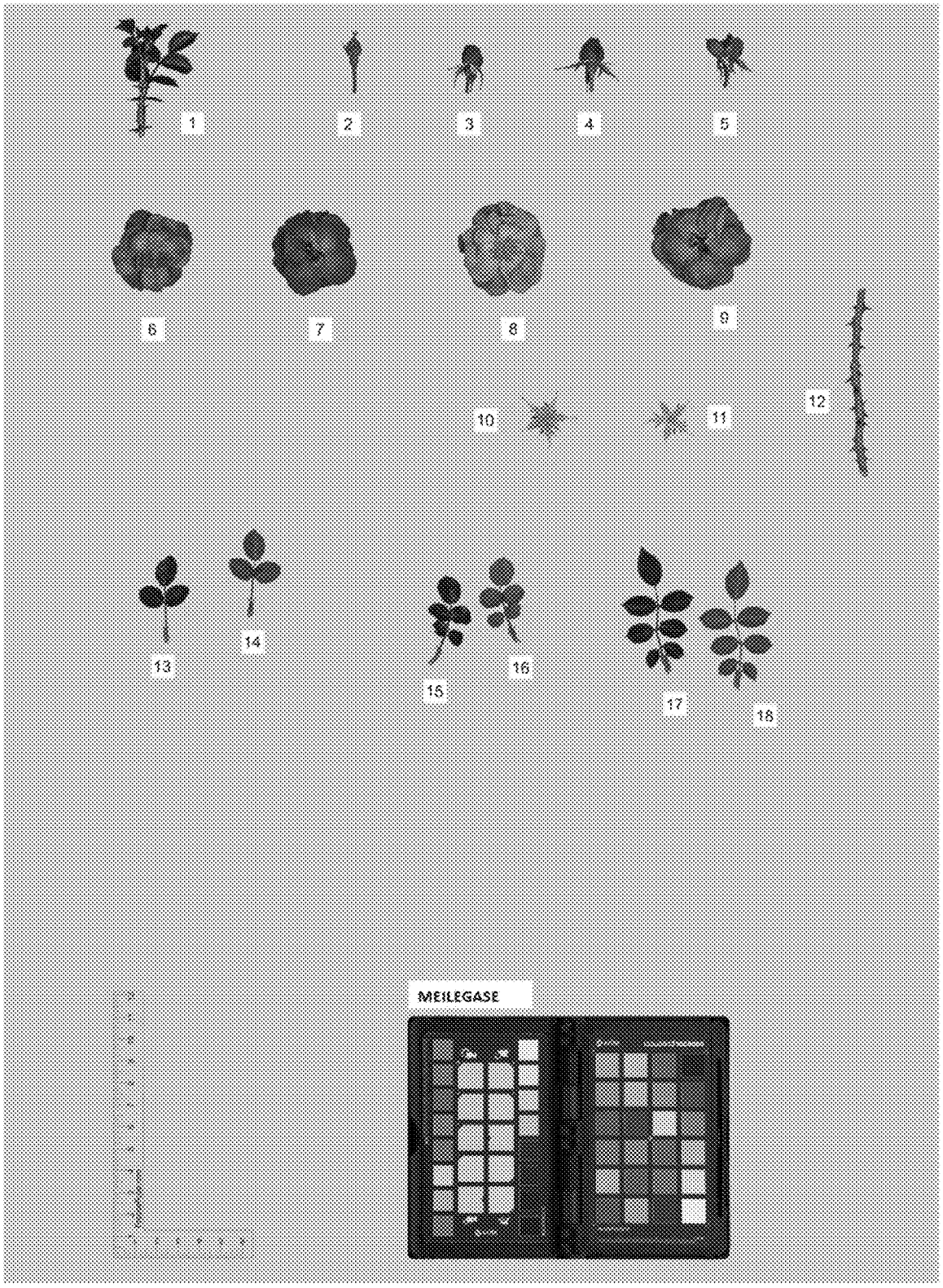
1
2
3
4
5
6
7
8
9
10
11
12
13
14
15
16
17
18
MEILEGASE